United States Patent [19]
Wong

[11] Patent Number: 5,490,782
[45] Date of Patent: Feb. 13, 1996

[54] PREFORMED POSTERIOR PALATEL SEAL FOR EXISTING DENTURES AND METHOD

[76] Inventor: Nelson J. Wong, 2101 Midway Rd., Suite 250, Carrollton, Tex. 75006

[21] Appl. No.: 182,810

[22] Filed: Jan. 14, 1994

[51] Int. Cl.$^6$ ................................................. A61C 13/00
[52] U.S. Cl. ........................... 433/167; 433/213; 433/184
[58] Field of Search .............................. 433/167, 168.1, 433/171, 199.1, 213, 184, 188

[56] References Cited

U.S. PATENT DOCUMENTS

| | | |
|---|---|---|
| 514,201 | 2/1894 | Robertson . |
| 729,621 | 3/1903 | Malone . |
| 1,729,461 | 9/1929 | Thayer . |
| 2,101,431 | 12/1937 | Groff . |
| 2,171,736 | 9/1939 | Ballard . |
| 2,663,933 | 12/1953 | Avery ................................ 433/168.1 |
| 2,768,440 | 10/1956 | Elliott . |
| 2,985,961 | 5/1961 | Schwartz . |
| 3,335,495 | 8/1967 | Wichner . |
| 3,464,111 | 9/1969 | Gillard . |
| 3,567,806 | 3/1971 | Dyal ........................................ 264/18 |
| 3,621,575 | 11/1971 | Schneider et al. . |
| 3,644,996 | 2/1972 | Weinkle . |
| 3,667,123 | 6/1972 | Huey . |
| 3,783,514 | 1/1974 | Kersten . |
| 3,839,796 | 10/1974 | Hazar . |
| 3,846,911 | 11/1974 | Wichner . |
| 4,017,971 | 4/1977 | Hazar ............................................. 32/2 |
| 4,019,253 | 4/1977 | Hazar ........................................... 32/19 |
| 4,097,992 | 7/1978 | Hazar ............................................. 32/2 |
| 4,161,065 | 7/1979 | Gigante ..................................... 264/18 |
| 4,247,287 | 1/1981 | Gigante ..................................... 433/199 |
| 4,337,042 | 6/1982 | von Nostitz ............................. 433/171 |
| 4,370,133 | 1/1983 | Stempel .................................. 433/171 |
| 4,470,815 | 9/1984 | Hazar ..................................... 433/171 |
| 4,583,947 | 4/1986 | Hazar ..................................... 433/171 |
| 4,932,869 | 6/1990 | Bergeron ................................ 433/167 |

OTHER PUBLICATIONS

"Richard W. Brand and Donald E. Isselhard, Oral Cavity Proper," *Anatomy of Orofacial Structures*, (St. Louis: The C. V. Mosby Company, 1977), pp. 333–335.

J. A. Hobkirk, "Decisions to be Made Before the Next Visit," *Complete Dentures*, (Surrey: Adlard & Son 1986), pp. 78–81.

Gino Passamonti, "Posterior Limit and Posterior Seal," *Atlas of Complete Dentures*, (Berlin: Quintessence Publishing Co., Inc., 1979), pp. 90–97.

David M. Wattt and A. Roy MacGregor, "Retention," *Designing Complete Dentures* (Surrey: Adlard & Son 1986), pp. 54–57, 198.

Marc Appelbaum, "The Posterior Palatal Seal," *Essentials of Complete Denture Prosthodontics*, (Philadelphia: W. B. Saunders Company 1979), pp. 171–192.

John D. Jones, "A Qualitative Comparison of Various Record Base Materials," *The Journal of Prosthetic Dentistry*, 49, No. 1, Jan. 1983–pp. 130–132.

Joseph Nassif and Russell Jumbelic, "Duplicating Maxillary Complete Dentures," *The Journal of Prosthetic Dentistry*, 52, No. 5 Nov. 1984, pp. 753–755.

Hyman Kotkin, "Diagnostic Significance of Denture Complaints," *The Journal of Prosthetic Dentistry*, 53, No. 1, Jan. 1985, pp. 73–77.

Joe H. Jaggers, Nikzad S. Javid and Frank A. Colaizzi, "Complete Denture Curriculum Survey of Dental Schools in the United States," *The Journal of Prosthetic Dentistry*, 53, No. 5, May 1985 pp. 736–739.

(List continued on next page.)

*Primary Examiner*—Cary E. O'Connor
*Attorney, Agent, or Firm*—John W. Montgomery; Ross, Clapp, Korn & Montgomery

[57] ABSTRACT

A preformed posterior palatal seal (Preformed PPS) for securing to, anatomically based existing dentures includes a body preformed of a predetermined size and shape of a posterior palatal seal (PPS) for sealing an existing denture at the "Ah line" of the human palate and adhesive for holding the preformed body to a denture.

15 Claims, 4 Drawing Sheets

OTHER PUBLICATIONS

Bernard Levin and John L. Sanders, "Results of a Survey of Complete Denture Procedures Taught in American and Canadian Dental Schools: An Update," *The Journal of Prosthetic Dentistry*, 54, No. 2, Aug. 1985, pp. 302–306.

Arthur Nimmo, "Correction of the Posterior Palatal Seal By Using a Visible Light–Cured Resin: A Clinical Report," *The Journal of Prosthetic Dentistry*, 59, No. 5, May 1988, pp. 529–531.

W. P. Naylor and J. D. Rempala, "The Posterior Palatal Seal–Its Forms and Functions (II)–Design and Cast Preparation," *QDT* (Quintessence of Dental Technology), 10, No. 8, Sep. 1986, pp. 489–492.

W. Patrick Naylor and Vincent A. Stephens, "Location and Transfer of the Vibrating Line: Clinical and Laboratory Techniques," *QDT* (Quintessence of Dental Technology), 10, No. 9, Oct. 1986, pp. 557–559.

J. A. von Fraunhofer, Z. Khan and R. Razavi, "The Effect of the Posterior Palatal Seal on the Strength of Maxillary Denture Bases," *QDT* (Quintessence of Dental Technology), 11, No. 3, Jun. 1987, pp. 193–194.

Hiroshi Muraoka, "Adding a Posterior Palatal Seal," *A Color Atlas of Complete Denture Fabrication* (Tokyo: Quintessence Publishing Company, 1989), pp. 6, 409–412.

Robert M. Morrow, Kenneth D. Rudd and John E. Rhoads, "Posterior Palatal Seal," *Dental Laboratory Procedures* (St. Louis: The C. V. Mosby Company, 1986), pp. 125–128.

Judson C. Hickey, George A. Zarb and Charles L. Bolender, "Perfection of the Posterior Palatal Seal," *Prosthodontic Treatment for Edentulous Patients* (9th Ed.) (St. Louis: The C. V. Mosby Company, 1985), pp. 422–426.

Marc Appelbaum, "The Posterior Palatal Seal," *Essentials of Complete Denture Prosthodontics* (2nd Ed.) (Massachusetts: PSG Publishing Company, 1984), pp. 107–122.

Bernard Levin, "Completion of Master Casts and Carving the Posterior Palatal Seal," *Impressions for Complete Dentures* (Chicago: Quintessence Publishing Company, Inc., 1984), pp. 143, 147, 150–161, 168–170 and 180–186.

William E. Avant, "A Comparison of the Retention of Complete Denture Bases Having Different Types of Posterior Palatal Seal," *The Journal of Prosthetic Dentistry*, 29, No. 5, May 1973, pp. 484–493.

A. A. Calomeni, E. E. Feldmann and W. A. Kuebker, "Posterior Palatal Seal Location and Preparation on the Maxillary Complete Denture Cast," *The Journal of Prosthetic Dentistry*, 49, No. 5, May 1983, pp. 628–630.

Frank R. Lauciello and Salvatore P. Conti, "A Method of Correcting the Posterior Palatal Seal Area of a Maxillary Complete Denture," *The Journal of Prosthetic Dentistry* (vol. 42, No. 6) Dec. 1979–pp. 690–692.

Ernest A. Carroll and Francis W. Shaffer, "Redefining the Posterior Palatal Seal on a Complete Denture," *The Journal of Prosthetic Dentistry*, 43, No. 1, Jan. 1980, pp. 105–107.

Gerald N. Graser, "Review of the Literature: Predoctoral Removable Prosthodontics Education," *The Journal of Prosthetic Dentistry*, 64, No. 3, Sep. 1990, pp. 326–333.

Glossary of Prosthodontic Terms, *The Journal of Prosthetic Dentistry*, 58, No. 6, Dec. 1987, p. 750.

Kenneth B. May, Michael E. Rozzoog, Andrew Koran III and Emerson Robinson, "Denture Base Resins: Comparison Study of Color Stability," *The Journal of Prosthetic Dentistry*, 68, No. 1, pp. 78–82.

Joe H. Jaggers, Nikzad S. Javid and Frank A. Colaizzi, "Complete Denture Curriculum Survey of Dental Schools in the United States," *The Journal of Prosthetic Dentistry*, 53, No. 5, May 1985, pp. 736–739.

Dale E. Smith, "Color Stability of Long–Term Soft Denture Liners," *The Journal of Prosthetic Dentistry*, 68, No. 5, Nov. 1992, pp. 836–838.

Zafrulla Khan and C. Brent Haeberle, "One–appointment Construction of an Immediate Transitional Complete Denture Using visible Light–Cured Resin," *The Journal of Prosthetic Dentistry*, 68, No. 3, Sep., 1992, pp. 500–502.

Dale E. Smith, "Annual Review of Selected Dental Literature: Report of the Committee on Scientific Investigation of the American Academy of Restorative Dentistry," *The Journal of Prosthetic Dentistry*, 70, No. 1, Jul. 1993, pp. 44, 78 and 85.

Jay Steinberg, "A Teaching Aid for the Visualization of the Posterior Palatal Seal Using a Modified Base Tray," *The Journal of Prosthetic Dentistry*, 67, No. 6, Jun. 1992, pp. 897–899.

G. Gauthier, J. E. Williams and J. D. Zwemer, "The Practice of Complete Denture Prosthodontics by Selected Dental Graduates," *The Journal of Prosthetic Dentistry*, 68, No. 2, Aug. 1992, pp. 308–313.

W. D. Schwarz, "The Post Dam," *Dental Update*, 18, No. 18, Jan./Feb. 1991, pp. 26–30.

"How to Bond Acrylic to Metal in Three Minutes (and why you'd want to)," advertisement for 4–META Solder starter kit (one–page).

Carol A. Lefebvre, Kent L. Knoernschild and Arthur O. Rahn, "Enhancing Retention in Complete Dentures for Patients with Atypical Muscle Attachments: Case Reports," *Quintessence International*, 24, No. 10, 1993, pp. 753–755.

Carton containing 12 EZO Upper Heavy Denture Cushions (U.S. Pat. No. 2,897,593) (front and back views of carton).

"JELENKO Dental Health Products Catalog: Table of Contents (pp. 2–3), Waxing" section of Merchandise (pp. 36–38) and Price List (pp. 10–11) (1993).

NOBILIUM COMPANY Products Catalog: Plastic Preforms & Waxes section (pp. 11–15).

NOBILIUM COMPANY Catalog Supplement.

AUSTENAL, INC. Laboratory Products Price List, Effective Apr. 1991, p. 1; Insert to Price List, "PATTERNS".

AUSTENAL, INC. Sealon Anatomical Patterns, Upper Labio–Buccal Patterns and Lower Labio–Buccal Patterns.

PREFORMED POSTERIOR PALATEL SEAL FOR EXISTING DENTURES AND METHOD

TECHNICAL FIELD OF THE INVENTION

The present invention relates to devices and methods that facilitate formulation of posterior palatal seals (PPS) on upper dentures and particularly, to devices and molding processes by which effective PPS may be formed.

BACKGROUND OF THE INVENTION

Millions of people throughout the world, including as many as twenty million Americans are edentulous (toothless) and rely on full dentures for function and esthetics. In fabricating dentures, it is crucial for the dentist to assure that the upper denture is well-fitted and secure. This is important not only in speech and mastication, but also in avoiding the embarrassment of a loose or falling denture.

A secure denture is usually accomplished by the denture adapting well to the gum tissue, and in the case of the upper member of dentures, through the use of a posterior palatal seal (PPS). The combination of a well-fitting denture and a well-fitting PPS will create suction or vacuum once the upper denture is seated in the mouth. A PPS is a thickened posterior portion of the upper denture border extending across the palate from the left to the right maxillary tuberosity. The increased thickness of the denture along a narrow border adds "pressure" on the tissue and maintains a vacuum seal. Without this sealing effect created by the PPS, the upper denture "leaks" (the vacuum between the denture and the roof of the mouth is reduced or lost) and the denture loosens as the wearer talks, chews or swallows.

A PPS is beneficial and considered necessary by many dentists because the border of the upper denture at the posterior palate area rests on the junction between the hard and soft palate. Unless there is additional pressure against that area of the palate, there will be loss of suction during function. Anatomically, the key effective sealing area corresponds to the junction between the hard and soft palate. Among dentists, this is also called the "Ah-Line." In locating how far a denture should extend backwards, the dentist may ask the patient to repeat the "ah" sound. In doing so, the soft palate vibrates and the hard palate does not vibrate so that the demarcation between the soft and hard palate is discernible. This is typically where the denture border will lie. The junction between the hard and soft palate where the denture border lies is neither a straight line nor of uniform consistency. It is harder in the midline and soft on both sides of the midline. A well constructed PPS, therefore, has to reflect the anatomy and features of that part of the mouth.

Presently, the most common method of fabrication of the PPS requires either a dentist or a laboratory technician to carve an indentation channel on a plaster model obtained from an impression of the toothless mouth. The impression material is typically alginate, silicon, zinc oxide-eugenol or a rubber base material. The dentist normally takes an impression of the edentulous mouth and often prepares a plaster (or dental stone) model from the impression by pouring wet plaster onto the impression. Alternatively, the impression is boxed and sent to a dental lab for preparation of a plaster or dental stone model. When the plaster has set hard, it is separated from the impression. Either a dentist or a lab technician then carves an indentation on the plaster model where the PPS will be. The depth of carvings for the PPS preferably corresponds to the anatomical qualities of the area of the palate mentioned above. That is, to be an effective seal, less must be carved away from the midline where the palate tissue is hard and more on both sides of the midline where the palate tissue is softer. The carved portion is gradually deepened as it reaches the posterior border. If all goes well, the carving results in a "Cupid's Bow" like appearance with the "string" part of the bow at the denture border and the "serpentine bow" towards the front part of the mouth. Shallowest at the "serpentine bow", it deepens going towards the "string" of the bow (at the border of the denture) with the deepest on both sides of the midline and shallower at the midline of this "bow" and also the two ends of this "bow." If the "carver" lacks skill or if short cuts are taken, a simple groove might be carved or a denture might be formed without a PPS of any kind.

Carving methods are taught in practically every dental school and various shapes of PPS are practiced by most denture technicians. The carving method for forming a good PPS is tedious, time-consuming and the results are inconsistent. Some technicians simply carve a trench instead of a bow shape or another approximation of a "Cupid's bow" shape either because it saves time, because they lack a high degree or skill, or because they do not understand oral anatomy and physiology. The method of hand carving a "Cupid's bow" continues to be described and recommended by professors at reputable dental schools and major international journal articles, as for example in *Quintessence, Int.*, 1993; 24: 753–755.

Another less prevalent method of forming a PPS is termed a functional method or a waxing method. This method if currently more tedious and more time-consuming than the carving method. During an impression visit, the dentist applies a wax material on the impression in the poster palatal area of the impression. Again, a Cupid's bow shape provides an effective seal. A special wax is used which liquifies at mouth temperature and solidifies at room temperature. The wax is carefully shaped as by dabbing, brushing or otherwise placing it bit-by-bit and smoothing it onto the impression along the identified "Ah line." The impression is reinserted into the patient's mouth and held for several minutes to allow partial liquification and plastic deformation into and along the actual functional border between the hard and soft palate. The impression is then removed and carefully boxed to ship it to the dental lab for pouring of a plastic or a dental stone mold from which a denture will be molded. The wax must be maintained in a solidified condition during pouring so that a PPS channel will be formed in the mold. This channel in the mold will result in a raised PPS in the molded denture.

The process of forming a PPS on an existing denture has many steps and is time-consuming. The technician has to lubricate the denture; pour up a plaster model onto the denture; separate the model from the denture; carve the needed void for the PPS from the plaster model as described earlier; lubricate the model so that new denture material will not stick to the model; place new denture material into the carved void between the model and the denture; apply pressure so there is intimate contact between the new material and the denture base; wait for chemical bonding and curing of the new material; separate the denture from the model; and smooth and polish it for delivery to wearer.

SUMMARY OF THE INVENTION

The present invention uniquely provides a Preformed Posterior Palatal Seal (Preformed PPS) for use in upper dentures which can be applied onto existing dentures. Methods of applying the Preformed PPS are also provided existing denture applications.

The shape of the Preformed PPS advantageously corresponds consistently to the quality and anatomy of the oral tissue. Preferably, the Preformed PPS is thinner toward the front of the mouth and thicker at the rear border end. It is also preferably thinner at the mid-palate as human palate tissue is thin and bony and cannot be subjected to undue pressure from too much denture thickness. Thus, the PPS can be shaped like the Cupid's bow consistently. Variations in size and proportion according to size of the roof of the mouth may be accommodated with several sizes of Preformed PPS. The vault form of the individual mouth will be naturally accommodated by the flexibility and pliability of the Preformed PPS.

In use with ill-fitting dentures where the PPS area of the denture is weak or inadequate, the Preformed PPS is either soft, semi-hard or hard depending on the situation and corresponding best remedy to the inadequate PPS seal. In one embodiment, the Preformed PPS is made of material which bonds and cures chemically. In another embodiment, a light-cured method is employed to secure the Preformed PPS directly to dentures or denture reline material, e.g., methylmathacrylate or similar polymer. A hard Preformed PPS may be incorporated after any existing old PPS is ground off. Alternatively, a softer or more pliable Preformed PPS may be applied over an existing PPS to enhance and reshape the raised portion. In another embodiment, a Preformed PPS may be hard (or relatively harder) where it contacts the denture and soft (or relatively softer) where it contacts the tissue. In yet another embodiment, Preformed PPS may be provided to remedy situations where the denture border is short of the ideal rearward position, i.e., generally short of the junction between the hard and soft palate. Such an embodiment simultaneously extends the denture palate and creates a PPS which is bonded onto the existing inadequate denture.

Another advantage of a direct use Preformed PPS is where an existing denture is found to be inadequate apart from a poor PPS seal. This happens quite often even for previously well-fitting dentures because the underlying bone structure (ridge) changes over time. Without teeth, the alveolar bone, that previously supported teeth, atrophies after the teeth are gone. The denture does not change in dimensions over time but the underlying ridge shrinks allowing space and gaps to appear between the denture and the ridge, leading to looseness.

When a denture starts becoming loose, the dentist may decide not to fabricate a new denture but may decide to reline an existing denture. This is often done chair-side at the dental office. Without the Preformed PPS, the dentist would have to go through many steps, including taking an impression, pouring up the impression with dental stone or plaster, carving a void in the poured model and then filling the void with additional reline material similar to those steps mentioned earlier in order to incorporate a PPS. With a Preformed PPS instantly available, it is easy to see that the dentist can apply the Preformed PPS directly to the denture after the reline, bonding and curing the Preformed PPS directly in place, thus saving time and steps.

The human hand used in carving a plaster mold cannot consistently equal what this inventive Preformed PPS can generate without variation. It is an object of the invention to avoid repetitive laborious work in forming a new PPS with each denture. It is another object to obtain a consistently shaped PPS to maximize sealing with every denture created.

It is another object to provide a preformed PPS for use with indirect denture impressions. In a flexible form, the Preformed PPS is placed directly onto the denture impression taken from the patient's mouth. The Preformed PPS takes up the space for that part of the model which the technician would otherwise have to carve out of the plaster to create PPS, obviating the need of carvings by hand or time to sculpt a wax seal ridge and to allow it to mold itself as part of the impression, in the patient's mouth. Advantageously, a sufficient flexible preformed PPS can follow the contours of the denture impression so that a consistently uniform sealing pressure is naturally provided. Thus, even though the mouth and the resulting impression has its own contours, the seal raises proportionately in the appropriate places.

It is another object to provide a preformed PPS seal for use with direct denture seals. In a less flexible form, as for example, a Preformed PPS made of denture material or soft, yet preformed denture reline material, a Preformed PPS can be applied to an existing upper denture to correct an inadequate PPS (i.e., the dentist has ascertained leakage or inadequate vacuum seal in the patient's existing denture). The dentist or technician removes the old PPS and adds the new Preformed PPS constructed of denture material directly to the old denture. Since denture material, generally a polymer, such as methylmathacrylate, is chemically bondable to other denture materials, as in a process using a monomer bonding agent, the new Preformed PPS and old denture become one denture with an effective PPS.

It is another object to provide a Preformed PPS for use directly after relining an existing denture. In situations where the dentist decides that relining or re-basing is necessary in an existing denture, the Preformed PPS can be placed directly onto the newly relined denture. Furthermore, if a denture is found to be inadequate because the border does not reach back far enough to the junction between the soft and hard palate, a suitable Preformed PPS may be bonded at the old border to extend the denture border and to also provide a properly positioned PPS.

It is a further object to provide a self-adhesive Preformed PPS for self-application by denture wearers. This reduces the need for denture adhesives, paste, powders and gels. It reduces the daily ritual of clean-up and of such denture adhesives for a denture wearer with an inadequately formed PPS. Again, self-adhesive the Preformed PPS which is flexible, further facilitates following natural contours in existing dentures so that uniform sealing pressure results.

BRIEF DESCRIPTION OF THE DRAWINGS

These and other objects, features and advantages of the invention will become more evident with reference to the drawings in which like reference numerals represent like elements and in which.

DETAILED DESCRIPTION OF THE PREFERRED EMBODIMENT

Figure 1:
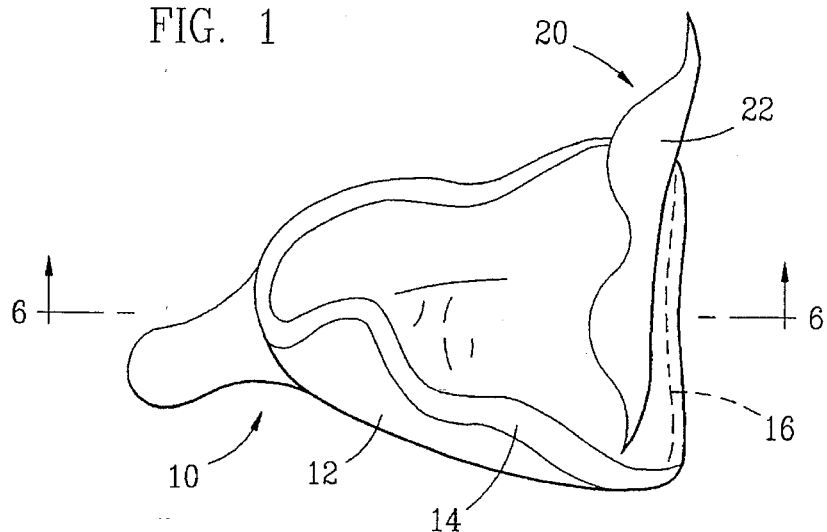
FIG. 1 is a perspective partially exploded view of an impression tray with an impression thereon for a complete denture with an embodiment of the inventive Preformed PPS shown in position for placement thereon.

FIG. 1 is a perspective view of a denture impression 10 showing one preferred embodiment of the Preformed PPS designated 20 in preparation to be placed thereon. Prior to taking this denture impression the dentist would fabricate an impression tray 12 which generally fits the contours and borders of the upper part of the edentulous mouth. Prior to taking this denture impression, the dentist would identify the "Ah-line", i.e., the junction between the hard and soft palate. The dentist asks the patient to repeat the sound "Ah", so that the vibration of the soft-palate thus initiated allows identification of the demarcation of the hard and soft palate. A marker generally of indelible ink is used to create a mark or line onto the patient's palate. While the impression is taken, the mark transfers onto the impression material 14. This is where the Preformed PPS 20 is placed so that the border of the Preformed PPS 20 coincides with the marker line 16 transferred thereon the impression material 14 on FIG. 1. Preferably, the Preformed PPS 20 has a body 22 which is in the shape of a "Cupid's bow," which shape has been found to provide a beneficial seal. Other known shapes for PPS could also be reproduced with the inventive Preformed PPS. However, the benefits of a "Cupid's bow" shaped PPS can be easily obtained by the dentist using the inventive Preformed PPS 20 without the additional carving and other steps previously required.

The denture impression 10 obtained with the "Ah-line" 16 identified as shown in FIG. 1 and with the inventive Preformed PPS 20 overlaid is thus made ready for pouring of a dental stone or a plaster, which will set in the dental impression 10. As mouth sizes vary with body size, various sizes of a Preformed PPS will be advantageous to conveniently allow construction of an effective PPS on any size denture. Preferably, three or four properly selected sizes corresponding to child, small, medium and large or other similar designations, as with standard denture molds or impression trays, could be used. The Preformed PPS 20 for this purpose should be of a pliable, flexible material, such as silicone or arginine, for example. A pliable flexible Preformed PPS will follow the contour of the impression so that it adds depth proportionately and a uniform pressure will result in the patient's mouth when a denture is formed using the Preformed PPS. As the impression is wet during handling, the Preformed PPS is preferably constructed to be able to adhere to or at least allow placement onto impression material which may be wet after removal from the patient's mouth. Thus, adhesives capable of adhesion under wet conditions may be used advantageously. In one embodiment, a separate adhesive material may be interposed between the Preformed PPS and the impression or a self-adhesive strip or tape material may be pre-formed or pre-applied directly onto the Preformed PPS. In a further preferred embodiment, the Preformed PPS may be provided with a removable non-stick sheet to prevent inadvertent sticking or it may be stored on a non-stick sheet until it is removed for application directly onto the denture impression.

Figure 2:
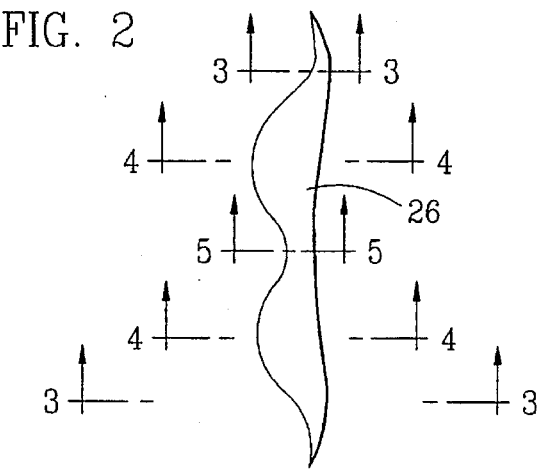
FIG. 2 is a top view of the inventive Preformed PPS as used in FIG. 1.

FIG. 2 shows a "Cupid's-bow" shaped Preformed PPS 20 from top view. A preferred shape of a Preformed PPS of this embodiment corresponds to anatomical features. The body 22 is thicker where the cross-sectional line 4—4 indicates and gradually less thick, both at mid-line, indicated by section lines 5—5 and also at the peripheral ends, represented by section lines 3—3.

Figure 3A:
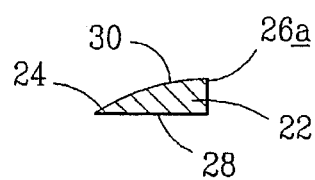
FIG. 3a is a cross-sectional view of a Preformed PPS as in FIG. 2 taken along line 3—3 showing one alternative shape.
Figure 3B:
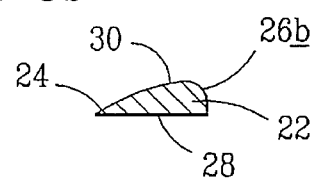
FIG. 3b is a cross-sectional view of a Preformed PPS as in FIG. 2 taken along line 3—3 showing another alternative shape.
Figure 4A:
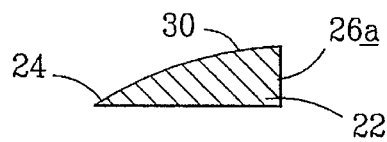
FIG. 4a is a cross-sectional view of a Preformed PPS as in FIG. 2 taken along line 4—4 showing one alternative shape.
Figure 4B:
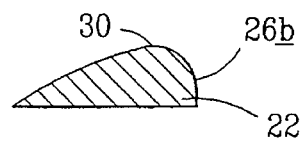
FIG. 4b is a cross-sectional view of a Preformed PPS as in FIG. 2 taken along line 4—4 showing another alternative shape.
Figure 5A:
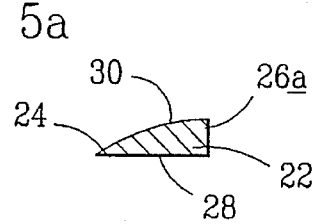
FIG. 5a is a cross-sectional view of a Preformed PPS as in FIG. 2 taken along line 5—5 showing one alternative shape.
Figure 5B:
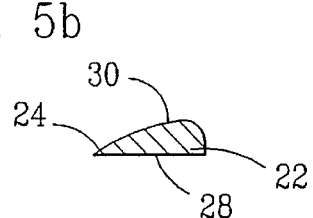
FIG. 5b is a cross-sectional view of a Preformed PPS as in FIG. 2 taken along line 5—5 showing another alternative shape.

Furthermore, the body 22 of the Preformed PPS 20 in the embodiment of FIG. 2 is tapered on side 24 towards the front (the hard-palate side of the seal). However, a rear side 26 towards the posterior denture border (the soft-palate side) is preferably formed at a right angle as shown at 26a by cross-sectional drawings in FIGS. 3a, 4a and 5a, or slightly rounded or slightly tapered according to an alternative embodiment as shown at 26b by cross-sectional drawings in FIGS. 3b, 4b and 5b. A flat base 28 of the Preformed PPS is provided for coming into contact with denture impression 14. Preferably, this base 28 will adhere to the denture impression as described above. The exposed face represented as 30, in both alternatives "a" and "b," is the face which is in contact with dental plaster or dental stone 32 when the impression is "poured" with fluid plaster or dental stone is poured into the impression 10 to form a denture model 34 as shown in FIGS. 7 and 8.

Figure 6:
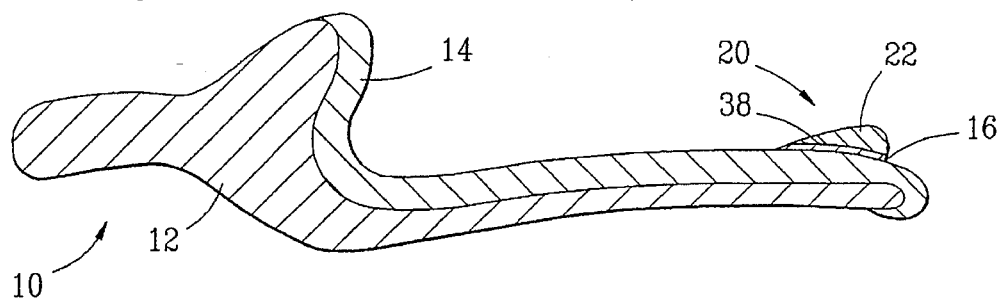
FIG. 6 is a cross-sectional view of the inventive Preformed PPS placed on an impression for complete dentures taken along section line 6—6 of FIG. 1.

FIG. 6 is a cross-sectional view of the Preformed PPS 20 placed onto the denture impression 10. The impression face 28 of the Preformed PPS (shown in FIGS. 3, 4 and 5) goes onto the impression 10 guided by the marker or line 16 indicating the "Ah-line", i.e., the demarcation of the hard and soft palate. The tapered side 24 of the Preformed PPS is positioned toward the front of the denture (the hard-palate side) whereas the denture border side 26 is positioned so that it lies on or near the line 16.

Figure 7:
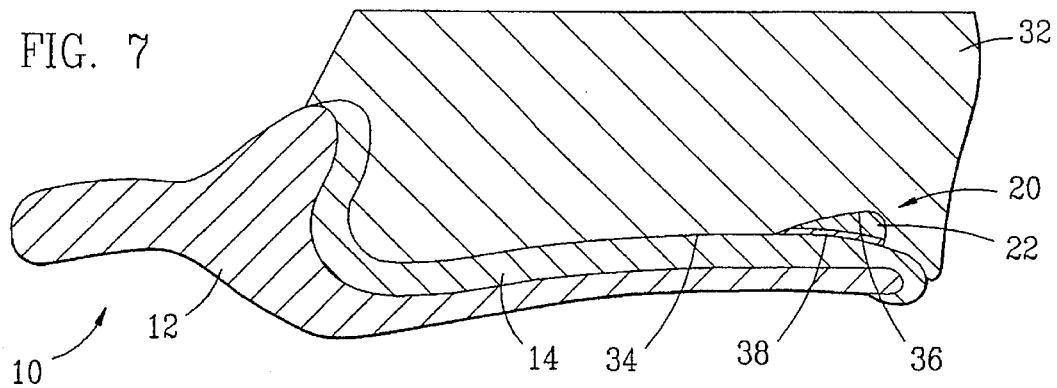
FIG. 7 is a cross-sectional view again taken along a center line of a denture impression with a dental stone poured onto the impression.
Figure 8:
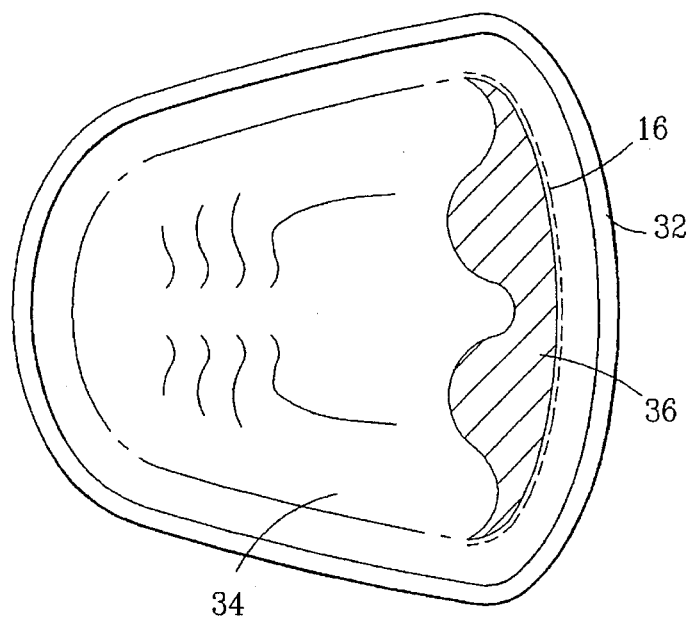
FIG. 8 is a bottom view of a dental stone model as in FIG. 7 after the stone model is separated from the impression where the inventive preformed PPS had been used.

After the Preformed PPS 20 is properly placed and dental stone 32 poured onto the impression 10 and allowed to set, the Preformed PPS 20 takes up the volume and forms a PPS channel 36, as shown in FIGS. 7 and 8, which will be occupied by a PPS when it is ultimately incorporated in a completed denture. The denture will be molded using the poured dental stone model 34 as a mold. The resulting raised area on the molded denture palate is merely polished and provides a suction or vacuum to be maintained when the denture is in place in the patient's mouth.

Another object is to provide a device for producing equal pressure along the seal, particularly a flexible seal which follows the terrain of the mold so that a consistent amount of pressure results.

FIG. 7 is a cross-sectional view of full denture impression similar to 10 in FIG. 3 where the Preformed PPS 20 is placed properly guided by the marker line 16. The Preformed PPS 28 is adhered to the impression material with an adhesive 38. Preferably, adhesive 38 is of a type which displaces water and adheres to either zinc oxide eugenol impression material or rubber-based impression material, even when it is wet as when it is removed from the patient's mouth after the impression is taken. Here, dental stone 32 is poured and allowed to set.

FIG. 8 is a bottom view (i.e., corresponding to the roof of the patient's mouth) of a dental model 34 similar to the one shown being formed in FIG. 7. Once the stone model 34 is separated from the impression 10, the Preformed PPS 20 has left its impression, void or PPS channel 36 as indicated at 36. The depth and contour of the PPS impression 36 or PPS channel 36 correspond to anatomical features of the mouth as needed for a proper PPS and an effective upper denture seal.

Figure 9:
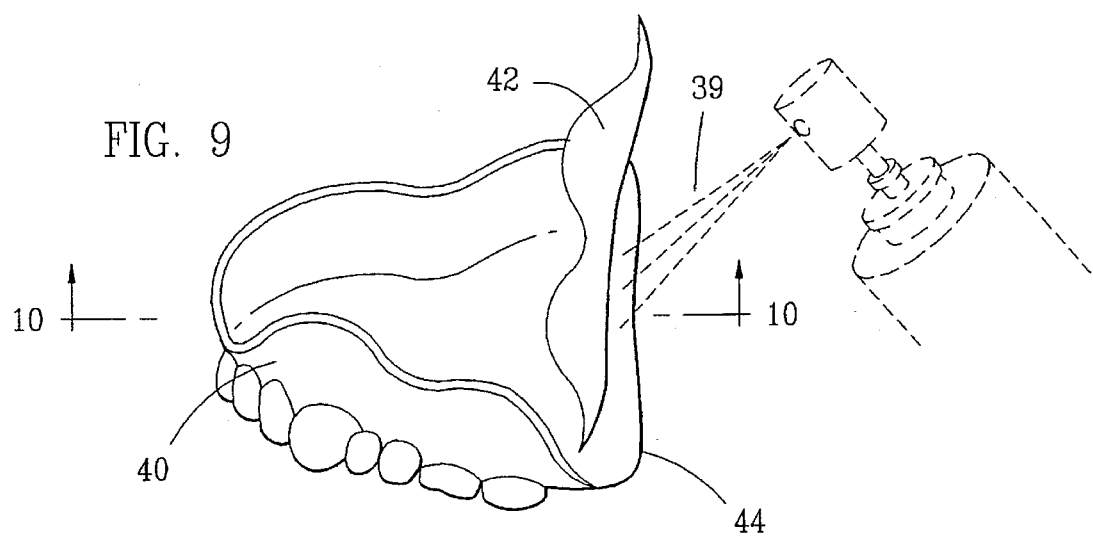
FIG. 9 is a schematic perspective view of an alternative embodiment of the inventive Preformed PPS showing a method for placement and for securing a Preformed PPS with a bonding agent onto an existing denture.

FIG. 9 is a perspective view of a denture 40 that is in need of a new PPS and an alternative embodiment of a Preformed PPS 42 in preparation to be placed thereon. The dentist would have first removed any previously existing old PPS and ascertain whether the denture border 44 in the palate area is properly extended to the patient's "Ah line" 16. If the denture border is too short, then an alternative embodiment of a Preformed PPS 46 of a kind that could extend the denture border would be used as seen in FIG. 11 following. If the denture border 44 is at the proper position, then a new Preformed PPS 42 would be placed and secured thereon either by polymerization chemically at 39, as shown schematically in FIGS. 9 and 10, or alternatively, through application of a light-curable material and subsequent light-curing action as shown in FIG. 11.

Figure 10:
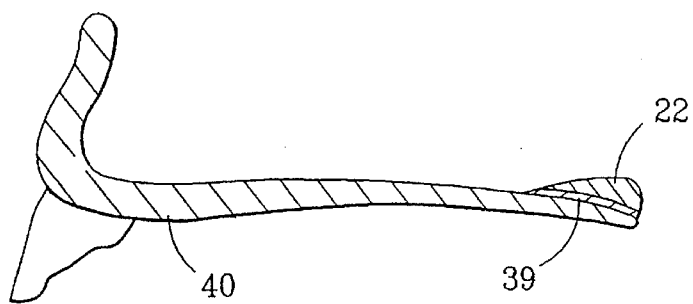
FIG. 10 is a cross-sectional view of the inventive Preformed PPS in use demonstrating a method to correct a poorly formed PPS, taken along section lines 10—10 of FIG. 9.
Figure 11:
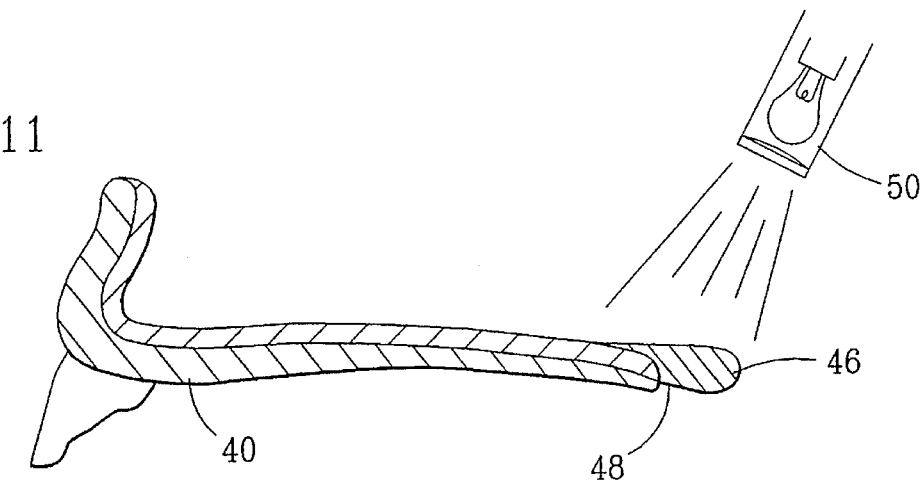
FIG. 11 is a cross-sectional view of yet another alternative embodiment of the Preformed PPS and method for using the new Preformed PPS to lengthen the border of the denture. The inventive Preformed PPS is of a kind that can be hardened by light-curing and the tip of the light unit is shown providing the light source.

FIG. 10 is a cross-section of the denture 40 along section lines 10—10 in FIG. 9. The old PPS has been ground off and a new Preformed PPS 42 has been incorporated thereon.

FIG. 11 is a cross-sectional view of a denture 40 which the dentist has completed a reline 48. The reline material 48 indicated, only renews that part of the denture that intimately touches the mouth. The reline material does not automatically create a new PPS. In the scenario shown in FIG. 11, not only is the old denture in need of a reline but also the PPS area is short of the "Ah-line". In this embodiment of the inventive Preformed PPS 46, a new PPS may be easily obtained by simply using a Preformed PPS 46 that is wider to actually extend the border of the denture to reach backwards towards the soft-palate at the "Ah-Line". Furthermore, Preformed PPS 46 is slightly thicker and harder in consistency as it does not rest on the denture but instead creates a new extension of the denture border. In this alternative embodiment, the Preformed PPS 46 is placed at its desired position to extend the denture border and to create a new PPS. A light source is shining on the Preformed PPS 46 to initiate polymerization. In this embodiment, a new PPS may be incorporated chair-side simply and effectively to salvage an ill-fitting denture with a poor PPS seal.

Figure 12:
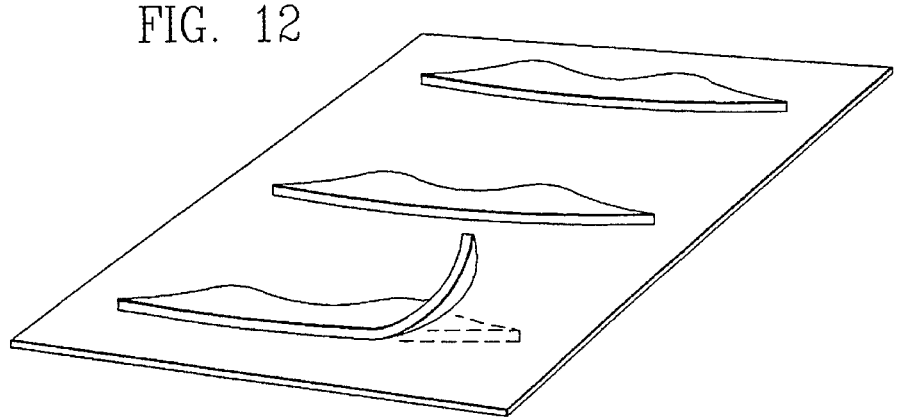
FIG. 12 is a perspective view of a self-adhesive Preformed PPS which may be applied by denture wearers to temporarily correct a malformed or an otherwise inadequate PPS until a visit to a dentist can be scheduled.

The embodiment shown in FIG. 12 provides one or more Preformed PPS devices having a self-adhesive material applied to the base. The dentist or the denture wearer merely removes a Preformed PPS and applies it temporarily to an existing denture to provide additional sealing. The body is preferably flexible or pliable so that the Preformed PPS conforms to the contours of the existing denture. Both the adhesive and the body material are water or moisture-resistant so that continuous or repeated exposure to the mouth tissues will not deteriorate them. The adhesive and the pliable body material are also non-toxic, such as rubber or plastic material. Each Preformed PPS may be provided with its own non-adhesive backing sheet to prevent it from becoming inadvertently adhered before intended. Alternatively, a plurality of Preformed PPS devices may be provided on an enlarged sheet having a non-adhesive or non-stick surface so that individual Preformed PPS devices may be removed and used as needed.

Particularly in embodiments where the Preformed PPS is used with an existing denture, the base 28 may be formed relatively harder than the face 30 which is softer for comfortable contact with the patient.

Other alterations and modifications of the invention will likewise become apparent to those of ordinary skill in the art upon reading the present disclosure, and it is intended that the scope of the invention disclosed herein be limited only by the broadest interpretation of the appended claims to which the inventors are legally entitled.

What is claimed is:

1. A Preformed Poster Palatal Seal (Preformed PPS) for use on existing dentures comprising:

(a) a body preformed with a predetermined, anatomically based size and shape of a posterior palatal seal (PPS) for sealing an upper denture and increasing pressure at the "Ah line" of a human palate; and (b) means for securing said preformed body to an existing denture at an anatomical position corresponding to the "Ah line" to form a posterior palatal seal thereon.

2. A Preformed PPS as in claim 1 wherein said body is composed of a substantially flexible polymer.

3. A Preformed PPS as in claim 2 wherein said means for securing said body to said denture comprises a thin layer of chemical bonding agent interposed between said body and said denture.

4. A Preformed PPS as in claim 2 wherein said means for securing said body to said denture comprises a layer of light curable bonding agent interposed between said body and said denture.

5. A Preformed PPS as in claim 1 wherein said body is composed of denture forming material.

6. A Preformed PPS as in claim 1 wherein said body is formed substantially in the shape of a Cupid's bow.

7. A Preformed PPS as in claim 1 wherein said body has a cross-sectional wedge shape thinner at an anterior side and thicker at a posterior side of said body and thinner at a midline and at buccal ends thereof so that it conforms to an anatomical configuration of a border between a hard palate and a soft palate.

8. A Preformed PPS as in claim 1 wherein said means for securing said body to said denture comprises a thin layer of adhesive.

9. A Preformed PPS as in claim 1 wherein said means for securing said Preformed PPS to said denture comprises a base portion of said body composed of fluid light-curable denture forming material bondable to said denture and curable with light after placement thereon.

10. A Preformed PPS as in claim 1 wherein said body is formed of a first hardness at a base to be secured to said existing denture and a second hardness which is softer than said first hardness at a face which is to contact a patient's palate.

11. A Preformed PPS as in claim 1 wherein said body is formed of a material which is sufficiently flexible to follow the existing contours of an existing denture.

12. A method of forming a posterior palatal seal on an existing denture comprising the steps of:

(a) positioning a preformed posterior palatal seal on said denture at an "Ah line;"

(b) applying a bonding agent between said Preformed PPS and said denture; and (c) allowing said bonding agent and bonded denture and Preformed PPS material to cure so that a PPS is formed on said denture.

13. A method of forming a posterior palatal seal on a denture as in claim 12 further comprising the step of removing an existing posterior palatal seal prior to applying a bonding agent between said Preformed PPS and said denture.

14. A method as in claim 12 wherein said step of applying said bonding agent further comprises a step of applying a chemical bonding agent.

15. A method as in claim 12 wherein said steps of:

(a) applying said bonding agent further comprises a step of applying a light-curable bonding agent; and (b) allowing said bonding agent to cure comprises the step of exposing said light-curable bonding agent to an appropriate light source to allow curing.

* * * * *

UNITED STATES PATENT AND TRADEMARK OFFICE
CERTIFICATE OF CORRECTION

PATENT NO. : 5,490,782
DATED : February 13, 1996
INVENTOR(S) : Nelson J. Wong It is certified that error appears in the above-identified patent and that said Letters Patent is hereby corrected as shown below:

On the title page, item [54], replace "Palatel" with —Palatal—.

In the Abstract:

Lines 2 and 3:

Immediately following "securing to", delete -- anatonically [sic] based --.

Immediately following "a predetermined", insert -- anatomically based --.

Column 1, Line 1:

Replace "Palatel" with -- Palatal --.

UNITED STATES PATENT AND TRADEMARK OFFICE
CERTIFICATE OF CORRECTION

PATENT NO. : 5,490,782
DATED : February 13, 1996
INVENTOR(S) : Nelson J. Wong

It is certified that error appears in the above-indentified patent and that said Letters Patent is hereby corrected as shown below:

Column 3, Line 1:

Immediately following "are also provided ...", insert —for—.

Signed and Sealed this

Eleventh Day of June, 1996

Attest:

BRUCE LEHMAN

Attesting Officer     Commissioner of Patents and Trademarks